US011903863B2

(12) United States Patent
Du et al.

(10) Patent No.: US 11,903,863 B2
(45) Date of Patent: Feb. 20, 2024

(54) SPLINT AND METHOD FOR OPERATING SPLINT

(71) Applicant: BOE TECHNOLOGY GROUP CO., LTD., Beijing (CN)

(72) Inventors: Zhihong Du, Beijing (CN); Wenbo Li, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 766 days.

(21) Appl. No.: 16/766,532

(22) PCT Filed: Nov. 13, 2019

(86) PCT No.: PCT/CN2019/117961
§ 371 (c)(1),
(2) Date: May 22, 2020

(87) PCT Pub. No.: WO2020/140621
PCT Pub. Date: Jul. 9, 2020

(65) Prior Publication Data
US 2021/0212853 A1 Jul. 15, 2021

(30) Foreign Application Priority Data
Jan. 2, 2019 (CN) .......................... 201910002440.3

(51) Int. Cl.
*A61F 5/058* (2006.01)
*G01L 5/10* (2020.01)
(Continued)

(52) U.S. Cl.
CPC ............ *A61F 5/05825* (2013.01); *G01L 1/00* (2013.01); *G01L 5/10* (2013.01); *H02K 11/20* (2016.01);
(Continued)

(58) Field of Classification Search
CPC .... A61F 5/0104; A61F 5/0106; A61F 5/0109; A61F 5/0118; A61F 5/05; A61F 5/058;
(Continued)

(56) References Cited

U.S. PATENT DOCUMENTS 5,042,177 A * 8/1991 Schoch ................ A43C 11/165
36/50.1
5,609,567 A 3/1997 Kennedy et al.
(Continued)

FOREIGN PATENT DOCUMENTS

CN 201631447 U 11/2010
CN 204521108 U 8/2015
(Continued)

*Primary Examiner* — Keri J Nelson
(74) *Attorney, Agent, or Firm* — Raj S. Dave

(57) ABSTRACT

A splint and a method for operating a splint are disclosed. The splint includes a plurality of plates, at least one rope, and at least one fastening drive device. The plurality of plates include a first plate. The rope is in movable connection with the plurality of plates. The fastening drive device is on the first plate, and is connected to the rope and configured to drive the rope under control, so as to allow the rope to be tightened or loosened under drive of the fastening drive device to drive the plurality of plates to move relatively close to each other or relatively away from each other.

19 Claims, 7 Drawing Sheets

(51) Int. Cl.
    *G01L 1/00*         (2006.01)
    *H02K 11/20*       (2016.01)
    *H02K 11/33*       (2016.01)
    *H10N 30/00*      (2023.01)
    *A61F 5/01*         (2006.01)

(52) U.S. Cl.
    CPC .............. *H02K 11/33* (2016.01); *H10N 30/00* (2023.02); *A61F 2005/0188* (2013.01)

(58) Field of Classification Search
    CPC .............. A61F 5/05825; A61F 5/05841; A61F 5/0585; A61F 5/05858; A61F 2005/0188; H02K 11/20; H02K 11/33; H10N 30/00; G01L 1/00; G01L 5/10
    See application file for complete search history.

(56) References Cited

U.S. PATENT DOCUMENTS

| | | | |
|---|---|---|---|
| 8,480,759 B2 * | 7/2013 | Pacanowsky | A61F 2/80 |
| | | | 623/36 |
| 9,839,553 B2 * | 12/2017 | Bannister | A61B 5/4833 |
| 2008/0039765 A1 * | 2/2008 | Nordt, III | A61F 5/32 |
| | | | 602/61 |

FOREIGN PATENT DOCUMENTS

| | | |
|---|---|---|
| CN | 208114689 U | 11/2018 |
| CN | 209316198 U | 8/2019 |

\* cited by examiner

SPLINT AND METHOD FOR OPERATING SPLINT

CROSS-REFERENCE TO RELATED APPLICATIONS

This application is the National Stage Entry of PCT/CN2019/117961 filed on Nov. 13, 2019, which claims priority of the Chinese Patent Application No. 201910002440.3, filed on Jan. 2, 2019, the entire disclosures of which are incorporated herein by reference as part of the disclosure of this application.

TECHNICAL FIELD

Embodiments of the present disclosure relate to a splint and a method for operating a splint.

BACKGROUND

In the medical field, gypsum is usually used to keep injured limbs of patients still, so as to protect the injured limbs and facilitate wound healing. For example, gypsum bandages and gypsum holders can be used for fixation. With the development of technologies, high polymer bandages and splints have been widely used and become the mainstream fixation manner in the medical field because of advantages of high strength, light weight, thin thickness, breathability, waterproofness, no skin allergy, X-ray transmission, easy disassembly, etc.

SUMMARY

At least one embodiment of the present disclosure provides a splint, and the splint includes: a plurality of plates, including a first plate; at least one rope, in movable connection with the plurality of plates; and at least one fastening drive device on the first plate, connected to the rope and configured to drive the rope under control, so as to allow the rope to be tightened or loosened under drive of the fastening drive device to drive the plurality of plates to move relatively close to each other or relatively away from each other.

For example, the splint provided by an embodiment of the present disclosure further includes a tension detecting circuit, and the tension detecting circuit is coupled to the rope and is configured to detect a tension applied to the rope.

For example, the splint provided by an embodiment of the present disclosure further includes a display, and the display is on one of the plurality of plates and in signal connection with the tension detecting circuit, and is configured to display a tension detecting result of the tension detecting circuit.

For example, in the splint provided by an embodiment of the present disclosure, the display includes a display screen or a pointer instrument panel.

For example, in the splint provided by an embodiment of the present disclosure, the rope includes a core wire that is conductive and an insulating sheath, and a cross section of the core wire is deformable under a tension, so as to allow a resistance of the core wire to change.

For example, in the splint provided by an embodiment of the present disclosure, a material of the core wire includes a piezoelectric ceramic fiber composite material or a conductive rubber.

For example, the splint provided by an embodiment of the present disclosure further includes a tension sensor, and the tension sensor is connected to the rope and is configured to deform under a function of a tension to allow a physical parameter of the tension sensor to change.

For example, in the splint provided by an embodiment of the present disclosure, the fastening drive device includes a driver and a fixer, the driver is connected to the rope, the fixer is connected to the first plate, and the driver is movable relative to the fixer.

For example, in the splint provided by an embodiment of the present disclosure, the driver includes a knob and a rope spool, the rope spool is connected to the rope, and the rope spool is capable of rotating along with the knob to allow the rope to be twined on the rope spool or unwound from the rope spool.

For example, in the splint provided by an embodiment of the present disclosure, the fixer includes a fixing shaft, the fixing shaft is fixed on the first plate, and the knob is capable of rotating around the fixing shaft.

For example, in the splint provided by an embodiment of the present disclosure, the fastening drive device further includes an electrical signal transmitter, the electrical signal transmitter includes a first conductive ring, a second conductive ring, a first electrical brush, and a second electrical brush, both the first conductive ring and the second conductive ring are on the fixing shaft, the first electrical brush is electrically connected to a first end of the rope and is in frictional and electrical connection with the first conductive ring, and the second electrical brush is electrically connected to a second end of the rope and is in frictional and electrical connection with the second conductive ring.

For example, in the splint provided by an embodiment of the present disclosure, in the case where the splint further includes a tension detecting circuit, the tension detecting circuit is coupled to the rope and is configured to detect a tension applied to the rope, and the first conductive ring and the second conductive ring are coupled to the tension detecting circuit.

For example, in the splint provided by an embodiment of the present disclosure, the driver includes a motor and a rope spool, the fixer includes a motor base, the rope spool is connected to the rope and is capable of rotating under drive of the motor to allow the rope to be twined on the rope spool or unwound from the rope spool, and the motor is on the motor base and connected to the rope spool, and is configured to rotate according to a driving signal to drive the rope spool to rotate, so as to allow the rope to be tightened or loosened.

For example, the splint provided by an embodiment of the present disclosure further includes a communication unit, and the communication unit is configured to receive a control signal that is wireless or wired and transmit the driving signal to the motor.

For example, in the splint provided by an embodiment of the present disclosure, the at least one rope includes a plurality of ropes, the at least one fastening drive device includes a plurality of fastening drive devices, and the ropes are connected to the fastening drive devices in one-to-one correspondence.

For example, the splint provided by an embodiment of the present disclosure further includes a power supply, and the power supply is on one of the plurality of plates and is configured to supply power to the tension detecting circuit and the display.

For example, in the splint provided by an embodiment of the present disclosure, the display is on the first plate.

For example, the splint provided by an embodiment of the present disclosure further includes a reminder device, and the reminder device is configured to perform a reminding operation in the case where a tension detecting result of the tension detecting circuit is less than a preset value.

For example, in the splint provided by an embodiment of the present disclosure, the rope is in movable connection with the plurality of plates in a parallel non-crossing manner or an S-shaped crossing manner.

At least one embodiment of the present disclosure further provides a method for operating the splint according to any one of the embodiments of the present disclosure, and the method includes: controlling the fastening drive device to allow the rope to be tightened or loosened, so as to allow the plurality of plates to fit a using object or separate from the using object which is in a space surrounded by the plurality of plates.

For example, in the method for operating the splint provided by an embodiment of the present disclosure, in the case where the splint further includes a tension detecting circuit and a display, the method further includes: adopting the tension detecting circuit to detect a tension applied to the rope, and adopting the display to display a tension detecting result of the tension detecting circuit.

BRIEF DESCRIPTION OF THE DRAWINGS

In order to clearly illustrate the technical solution of the embodiments of the present disclosure, the drawings of the embodiments will be briefly described in the following. It is obvious that the described drawings in the following are only related to some embodiments of the present disclosure and thus are not limitative of the present disclosure.

FIB. 5B is a partially enlarged view of a fastening drive device of the splint illustrated in FIG. 5A.

DETAILED DESCRIPTION

Figure 1A:
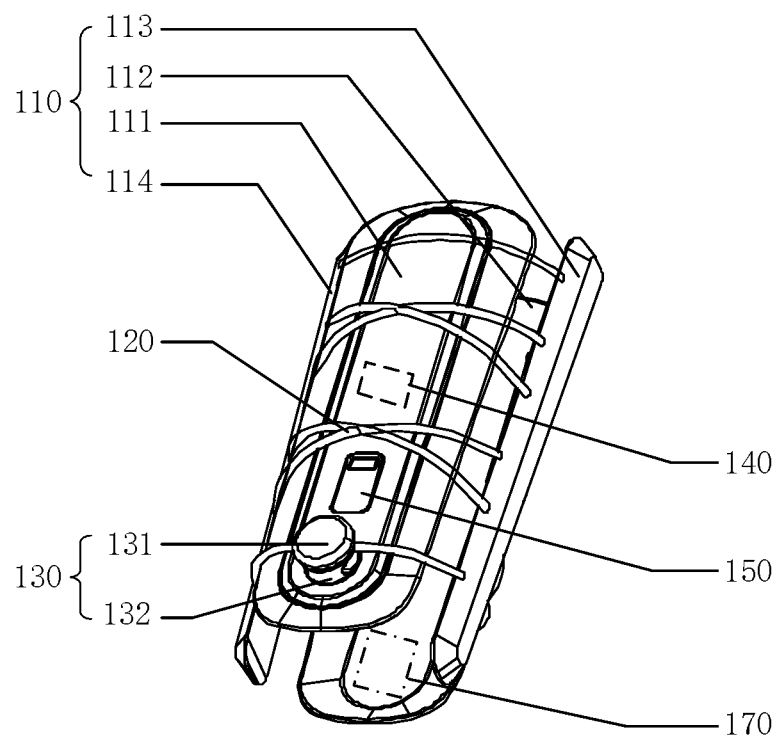
FIG. 1A is a schematic stereoscopic diagram of a splint provided by at least one embodiment of the present disclosure.

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment(s), without any inventive work, which should be within the scope of the disclosure.

Unless otherwise defined, all the technical and scientific terms used herein have the same meanings as commonly understood by one of ordinary skill in the art to which the present disclosure belongs. The terms "first," "second," etc., which are used in the description and the claims of the present application for disclosure, are not intended to indicate any sequence, amount or importance, but distinguish various components. Also, the terms such as "a," "an," etc., are not intended to limit the amount, but indicate the existence of at least one. The terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", "coupled", etc., are not intended to define a physical connection or mechanical connection, but may include an electrical connection, directly or indirectly. "On," "under," "right," "left" and the like are only used to indicate relative position relationship, and when the position of the object which is described is changed, the relative position relationship may be changed accordingly.

In the case where high polymer bandages and splints are used for fixation, a plurality of splints separated from each other need to be wrapped around the injured limb of the patient by using high polymer bandages. Therefore, splint wrapping is difficult and takes long time. Moreover, after fixing the splints, problems such as loosening and displacement are likely to occur, which not only affects the fixing effect of the splints, but also may cause secondary injury to the patient to aggravate the condition. In addition, frequent disassembly and binding of the splints increases the workload of medical staffs and reduces work efficiency.

At least one embodiment of the present disclosure provides a splint and a method for operating a splint. The splint enables the user to adjust and fix the splint simply and quickly, thereby reducing user's workload, improving work efficiency, improving user's experience, and facilitating fixation of the splint. Moreover, the splint provided by at least some embodiments can further monitor the degree of tightness.

Hereinafter, the embodiments of the present disclosure are described in detail with reference to the drawings. It should be noted that the same reference numerals in different drawings are used to refer to the same described elements.

At least one embodiment of the present disclosure provides a splint, and the splint includes a plurality of plates, at least one rope, and at least one fastening drive device. The plurality of plates include a first plate. The rope is in movable connection with the plurality of plates. The fastening drive device is on the first plate, and is connected to the rope and configured to drive the rope under control, so as to allow the rope to be tightened or loosened under drive of the fastening drive device to drive the plurality of plates to move relatively close to each other or relatively away from each other.

Figure 1B:
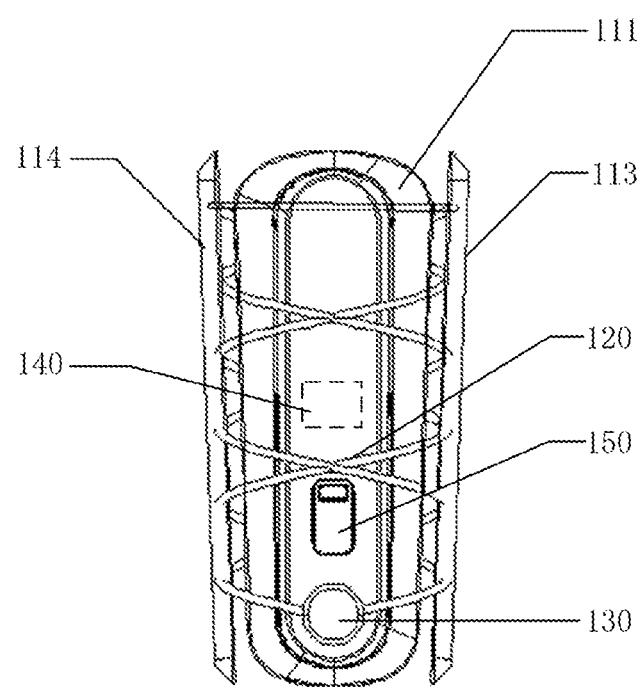
FIG. 1B is a front view of the splint illustrated in FIG. 1A.
Figure 1C:
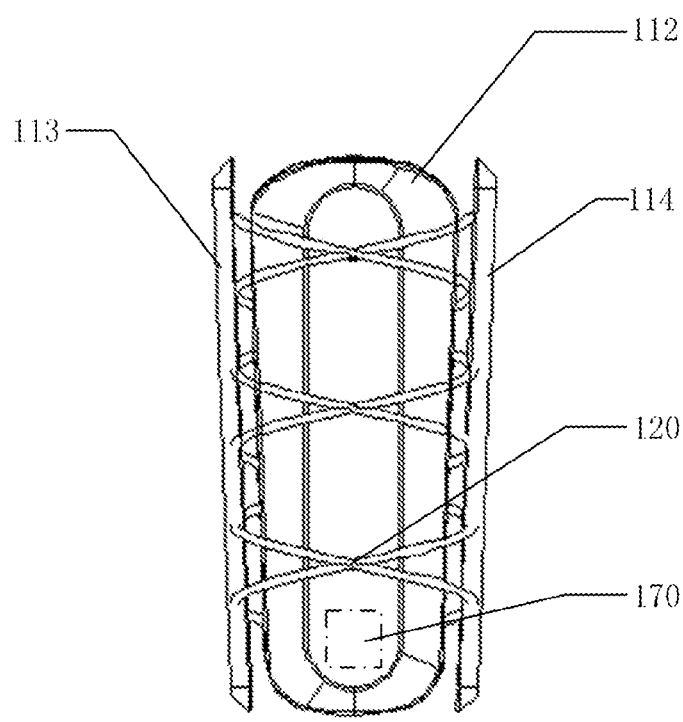
FIG. 1C is a rear view of the splint illustrated in FIG. 1A.

FIG. 1A is a schematic stereoscopic diagram of a splint provided by at least one embodiment of the present disclosure, FIG. 1B is a front view of the splint illustrated in FIG. 1A, and FIG. 1C is a rear view of the splint illustrated in FIG. 1A. As illustrated in FIG. 1A to FIG. 1C, a splint 100 includes a plurality of plates 110, a rope 120, and a fastening drive device 130.

The plurality of plates 110 of the splint 100 include a first plate 111, a second plate 112, a third plate 113, and a fourth plate 114. For example, the first plate 111 is opposite to the second plate 112, and the third plate 113 is opposite to the fourth plate 114. The space surrounded by the plurality of plates 110 can accommodate the injured limb of the patient, such as the leg, the arm, etc., so as to provide fixation and protection for the injured limb. For example, each plate may use a high polymer material, such as a glass fiber, polyurethane, a resin, etc., or may use other suitable materials, and the embodiments of the present disclosure are not limited in this aspect.

It should be noted that, in the embodiments of the present disclosure, the number of the plurality of plates 110 is not limited to 4 in the above case, but may also be other applicable quantities, such as 2 to 6, and the embodiments of the present disclosure are not limited in this aspect. The size of the plurality of plates 110 is not limited, and can be determined according to the size of the injured limb of the patient or according to empirical values. The sizes of the plurality of plates 110 may be the same or may be different from each other. For example, in an example, the first plate 111 and the second plate 112 have the same size, the third plate 113 and the fourth plate 114 have the same size, and the size of the first plate 111 or the second plate 112 is larger than that of the third plate 113 or the fourth plate 114. In this way, the plurality of plates 110 can better fit the injured limb of the patient, thereby providing better fixation, protection and other functions.

The rope 120 is in movable connection with the plurality of plates 110. For example, a plurality of through holes are provided on edges of the first plate 111, the second plate 112, the third plate 113, and the fourth plate 114, and the rope 120 passes through each of the through holes of the plates, so as to be in movable connection with the plurality of plates 110. For example, the rope 120 passes through the plurality of through holes in an S-shaped crossing manner or other applicable manners, and different manners may have different influences on the length of the rope 120, the fastening degree of the connection between the plurality of plates 110, and the like, which can be determined according to practical requirements.

The fastening drive device 130 is disposed on the first plate 111, and is connected to the rope 120 and configured to drive the rope 120 under control, so as to allow the rope 120 to be tightened or loosened under drive of the fastening drive device 130 to drive the plurality of plates 110 to move relatively close to each other or relatively away from each other. For example, the fastening drive device 130 includes a driver 131 and a fixer 132. The driver 131 is connected to the rope 120, and the fixer 132 is connected to the first plate 111. The driver 131 is movable relative to the fixer 132, and for example, the driver 131 can rotate relative to the fixer 132.

In the case where the driver 131 rotates relative to the fixer 132, the driver 131 drives the rope 120 to allow the rope 120 to be tightened or loosened, so that the plurality of plates 110 move relatively close to each other or relatively away from each other to adjust the size of the space surrounded by the plurality of plates 110. In the case where the rope 120 is loosened so that the plurality of plates 110 are relatively far away, the space surrounded by the plurality of plates 110 becomes larger, which is convenient for the injured limb of the patient to enter or move out of the space surrounded by the plurality of plates 110. In the case where the rope 120 is tightened, the plurality of plates 110 move relatively close to each other, the space surrounded by the plurality of plates 110 becomes smaller, which facilitates the fitting of the plurality of plates 110 to the injured limb of the patient, thereby providing fixation, protection and other functions.

The splint 100 enables the user to adjust and fix the splint simply and quickly, thereby reducing the user's workload, improving the work efficiency, and further improving the user's experience. Moreover, the splint 100 is formed as an integral structure, rather than a plurality of independent components. Compared with the traditional separating splint, the splint 100 is easy to store and is not easy to lose components in the case of not in use.

For example, the splint 100 further includes a tension detecting circuit 140. The tension detecting circuit 140 is coupled to the rope 120 and is configured to detect a tension applied to the rope 120. For example, the tension detecting circuit 140 may be provided on any one of the plates, for example, on the first plate 111.

Figure 2:
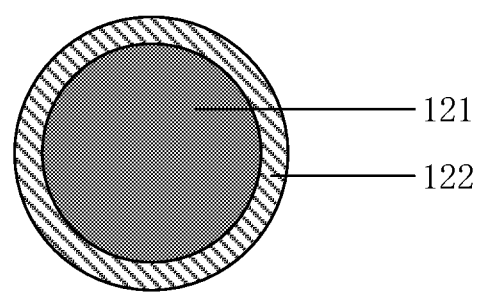
FIG. 2 is a schematic cross-sectional diagram of a rope of a splint provided by at least one embodiment of the present disclosure.

For example, in an example, in order to cooperate with the tension detecting circuit 140 to implement the tension detecting function, the rope 120 may adopt the structure illustrated in FIG. 2. The rope 120 includes a core wire 121 that is conductive and an insulating sheath 122, and a cross section of the core wire 121 is deformable under the function of a tension. For example, under the function of the tension, the area of the cross section of the core wire 121 becomes smaller, and the length of the core wire 121 becomes larger. The resistance calculation formula is:

$$R=\rho L/s,$$

where R represents the resistance value, p represents the resistivity, L represents the length, and S represents the area of the cross section. It can be obtained from the above formula that the resistance value of the core wire 121 changes under the function of the tension, and the amount of change in the resistance value is related to the degree of deformation of the core wire 121. For example, in the case where the tension increases, the resistance value of the core wire 121 increases; and in the case where the tension decreases, the resistance value of the core wire 121 decreases. For example, the specific relationship between the amount of change in the resistance value of the core wire 121 and the degree of deformation of the core wire 121 and the specific relationship between the degree of deformation and the tension value can be obtained through theoretical calculation or testing. Therefore, the tension detecting circuit 140 can be coupled (e.g., electrically connected) to the core wire 121 in the rope 120, so that the tension detecting circuit 140 can be used to detect the resistance value of the core wire 121, and the corresponding tension value can be obtained through analysis and calculation.

For example, the material of the core wire 121 may be a piezoelectric ceramic fiber composite material or a conductive rubber, or may be other suitable materials, which is not limited in the embodiments of the present disclosure. For example, the insulating sheath 122 wraps the core wire 121 for providing insulation, protection, etc., and any suitable materials such as rubber or plastic may be used.

Figure 3:
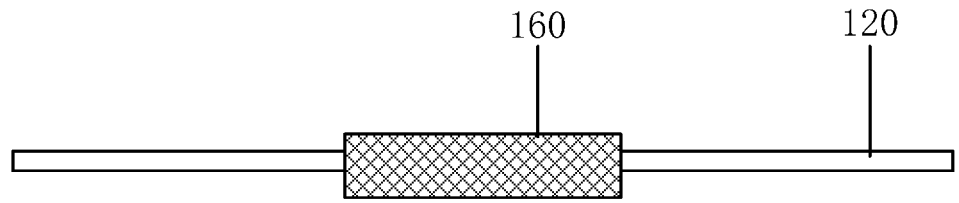
FIG. 3 is a schematic diagram of connection of a rope with a tension sensor in a splint provided by at least one embodiment of the present disclosure.

It should be noted that, in some examples, the rope 120 may also use materials without conductive properties, such as ordinary cotton, hemp, and nylon, and a tension sensor may be used to detect the tension. For example, as illustrated in FIG. 3, in an example, the splint 100 further includes a tension sensor 160, the rope 120 is connected to the tension sensor 160, and the tension sensor 160 is further coupled to the tension detecting circuit 140. The tension sensor 160 is configured to deform under the function of the tension, so that a physical parameter of the tension sensor 160 changes. Therefore, under the function of the tension, the physical parameter of the tension sensor 160 changes, so that the value of the physical parameter or the amount of change can be detected by the tension detecting circuit 140, and the corresponding tension value can be obtained through analysis and calculation. For example, the tension sensor 160 may be a deformable resistor, a deformable capacitor, etc., and accordingly, the physical parameter may be a resistance value, a capacitance value, etc., which is not limited in the embodiments of the present disclosure. The connection position of the tension sensor 160 and the rope 120 is not limited, and the tension sensor 160 can be connected to the rope 120 at any position in the rope 120.

It should be noted that, in the embodiments of the present disclosure, the tension detecting circuit 140 may be used to detect a resistance value, a capacitance value, or any other parameter, which can be determined according to the structure of the rope 120 or the type of the tension sensor 160, and the embodiments of the present disclosure are not limited in this aspect. The tension detecting circuit 140 may be implemented as the dedicated or universal electronic hardware (or circuit), such as a general resistance detecting circuit, a capacitance detecting circuit, etc., which is not limited in the embodiments of the present disclosure. For example, the tension detecting circuit 140 may further include a calculation processing circuit (for example, a processor) for calculating the corresponding tension value according to the detected resistance value, capacitance value, and other parameters. The specific configuration of the above electronic hardware is not limited, and may include analog components, digital chips, or other applicable components.

For example, the splint 100 further includes a display 150. The display 150 is provided on one of the plurality of plates 110, for example, on the first plate 111. The display 150 is in signal connection with the tension detecting circuit 140 and is configured to display a tension detecting result of the tension detecting circuit 140. For example, the tension detecting result includes one or more of the parameters such as the tension value, the recommended tension range, the indication of the degree of tightness, etc. The display 150 receives the tension detecting result transmitted by the tension detecting circuit 140 in a wired or wireless manner, and displays the tension detecting result in a suitable manner.

For example, the display 150 may be a display screen, a pointer instrument panel (such as a mechanical instrument or a digital tube), or other suitable display devices, and the embodiments of the present disclosure are not limited in this aspect. The display screen is, for example, an organic light-emitting diode (OLED) display screen, a liquid crystal display (LCD) screen, an electronic paper display screen, or the like. The size of the display 150 is not limited, and may be determined according to practical requirements, for example, according to factors such as the size of the plate and the amount of display content.

By using the tension detecting circuit 140 and the display 150, the splint 100 can facilitate the user to monitor the degree of tightness, and facilitate the user to adjust the appropriate degree of tightness and prevent the loosening of the splint 100, thereby improving the user's experience.

For example, the splint 100 further includes a power supply 170, and the power supply 170 is configured to supply power to the tension detecting circuit 140 and the display 150. The power supply 170 is provided on one of the plurality of plates 110, for example, on the second plate 112. For example, the power supply 170 is electrically connected to the tension detecting circuit 140 and the display 150 through electric wires (not illustrated in the figure). The power supply 170 can be a built-in power supply, such as a secondary battery (such as a lithium battery), a primary battery (such as an alkaline battery), a solar battery, or any other suitable power supply component, or can be an interface to an external power supply, and the interface is electrically connected to a power supply network through a wire, a transformer, or the like, which is not limited in the embodiments of the present disclosure.

It should be noted that, in some embodiments of the present disclosure, the positions of the fastening drive device 130, the tension detecting circuit 140, the display 150, and the power supply 170 are not limited to the case illustrated in FIG. 1A to FIG. 1C, and the fastening drive device 130, the tension detecting circuit 140, the display 150, and the power supply 170 can be respectively provided on any one of the plates. For example, in an example, as illustrated in FIG. 1A to FIG. 1C, the fastening drive device 130, the tension detecting circuit 140, and the display 150 are provided on the same plate (for example, the first plate 111), which may facilitate the user's operation and viewing, and may shorten the length of the wires used for electrical connection or signal connection between the various components, thereby improving the reliability. The power supply 170 is provided on another plate (such as the second plate 112) different from the above plate, which can provide a larger space for the power supply 170 and facilitate the use of the power supply component with greater storage capacity, thereby prolonging the standby time of the splint 100. For example, in some other embodiments, the power supply 170, the fastening drive device 130, the tension detecting circuit 140, and the display 150 may also be provided on the same plate, so as to facilitate power supply and avoid providing electrical wires between the plates. For example, the tension detecting circuit 140 may be integrated with the display 150 to reduce the number of components in the splint 100.

It should be noted that, in some embodiments of the present disclosure, the splint 100 may include more or fewer components, which may be determined according to practical requirements, and the embodiments of the present disclosure are not limited in this aspect. For example, in some embodiments, the tension detecting circuit 140, the display 150, and the power supply 170 may be omitted, and the splint 100 only includes the plurality of plates 110, the rope 120, and the fastening drive device 130. For example, in some other embodiments, the splint 100 may further include a reminder device (such as a buzzer), and the reminder device is configured to send a reminder to the user (e.g., a patient), for example, make an alarm, when the splint is loose, that is, when the tension detecting result of the tension detecting circuit 140 (e.g., the tension value detected by the tension detecting circuit 140) is less than a preset value.

Figure 4:
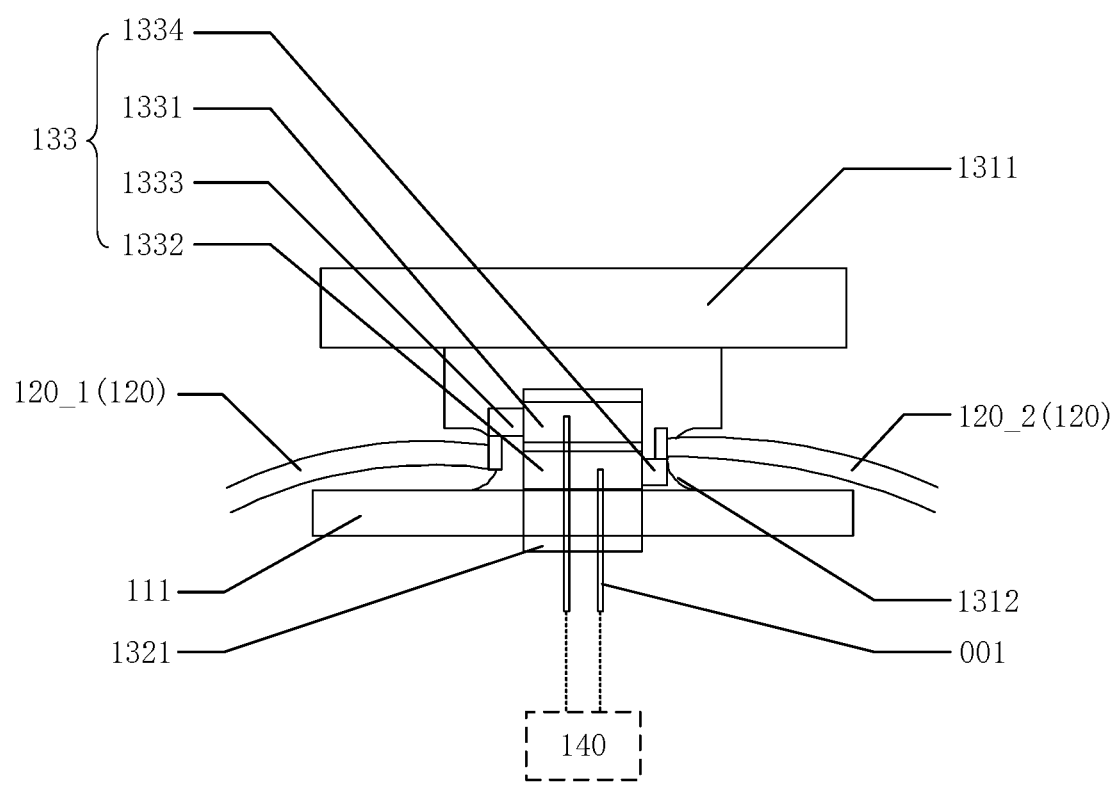
FIG. 4 is a partially enlarged view of a fastening drive device of the splint illustrated in FIG. 1A.

FIG. 4 is a partially enlarged view of a fastening drive device of the splint illustrated in FIG. 1A. As illustrated in FIG. 4, the driver 131 includes a knob 1311 and a rope spool 1312. The rope spool 1312 is connected to the rope 120, and the rope spool 1312 is capable of rotating along with the knob 1311 to allow the rope 120 to be twined on the rope spool 1312 or unwound from the rope spool 1312. For example, the knob 1311 may be a knob with a self-locking function or other suitable knobs, which is not limited in the embodiments of the present disclosure. The knob with the self-locking function can be referred to the conventional design, and details are not described herein. The rope spool 1312 is connected to a first end 120_1 and a second end 120_2 of the rope 120, respectively. For example, in an example, a plurality of through holes may be provided on the rope spool 1312, so that the first end 120_1 and the second end 120_2 of the rope 120 can pass through the plurality of through holes, respectively, and a snap ring and other components may be used to prevent the first end 120_1 and the second end 120_2 from falling off through the through holes. Certainly, the embodiments of the present disclosure are not limited to this case, and the rope spool 1312 may be connected to the first end 120_1 and the second end 120_2 of the rope 120 in other suitable manners. When the knob 1311 drives the rope spool 1312 to rotate, the rope 120 may be twined on the rope spool 1312 or unwound from the rope spool 1312, thereby allowing the rope 120 to be tightened or loosened to drive the plurality of plates 110 to move relatively close to each other or relatively away from each other.

For example, the fixer 132 includes a fixing shaft 1321, and the fixing shaft 1321 is fixed on the first plate 111. For example, the fixing shaft 1321 is located at the center of the knob 1311 and extends along the central axis of the knob 1311. The fixing shaft 1321 is used to provide a support shaft for the knob 1311, so that the knob 1311 can rotate around the fixing shaft 1321. For example, the connection manner of the fixing shaft 1321 and the knob 1311 may be determined according to the type and structure of the knob 1311, and the embodiments of the present disclosure are not limited in this aspect.

For example, in an example, in the case where the splint 100 further includes the tension detecting circuit 140 and the rope 120 which adopts the structure illustrated in FIG. 2, the fastening drive device 130 further includes an electrical signal transmitter 133. The electrical signal transmitter 133 is used to electrically connect the rope 120 to the tension detecting circuit 140. For example, the electrical signal transmitter 133 includes a first conductive ring 1331, a second conductive ring 1332, a first electrical brush 1333, and a second electrical brush 1334. Both the first conductive ring 1331 and the second conductive ring 1332 are provided on the fixing shaft 1321. The first electrical brush 1333 is electrically connected to the first end 120_1 of the rope 120, and is in frictional and electrical connection with the first conductive ring 1331. The second electrical brush 1334 is electrically connected to the second end 120_2 of the rope 120, and is in frictional and electrical connection with the second conductive ring 1332. Here, the electrical connection with the rope 120 and the electrical connection with the first end 120_1 or the second end 120_2 of the rope 120 refer to the electrical connection with the corresponding core wire 121.

When the knob 1311 drives the rope spool 1312 to rotate, the first end 120_1 and the second end 120_2 of the rope 120 also rotate along with the rope spool 1312, and the first electrical brush 1333 and the second electrical brush 1334 also rotate. Because the first electrical brush 1333 is in frictional and electrical connection with the first conductive ring 1331, and the second electrical brush 1334 is in frictional and electrical connection with the second conductive ring 1332, during the rotation, the rope 120 is electrically connected to the first conductive ring 1331 and the second conductive ring 1332 all the time. The core wire 121 in the rope 120 is in series connection between the first conductive ring 1331 and the second conductive ring 1332. For example, the first conductive ring 1331 and the second conductive ring 1332 are respectively coupled to the tension detecting circuit 140 through different electrical wires 001, so that the tension detecting circuit 140 can detect the resistance value of the core wire 121 in the rope 120, thereby implementing the tension detecting function.

Figure 5A:
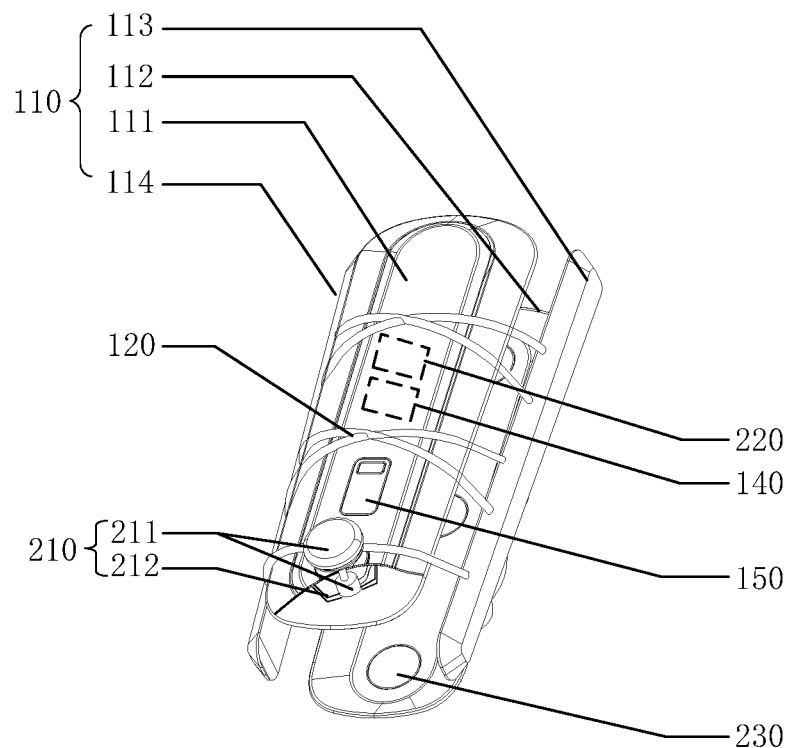
FIG. 5A is a schematic stereoscopic diagram of another splint provided by at least one embodiment of the present disclosure.
Figure 5B:
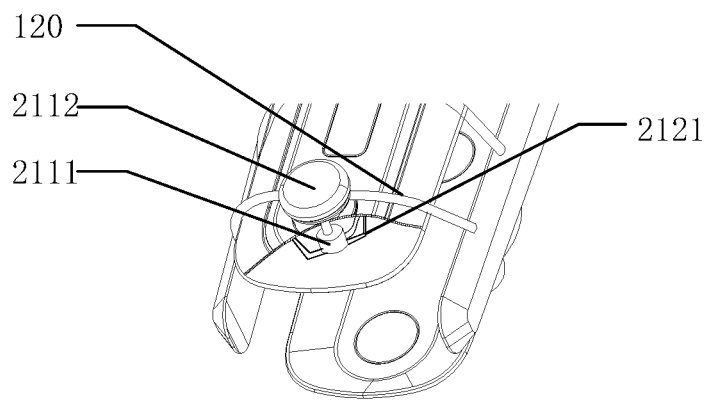

FIG. 5A is a schematic stereoscopic diagram of another splint provided by at least one embodiment of the present disclosure, and FIB. 5B is a partially enlarged view of a fastening drive device of the splint illustrated in FIG. 5A. As illustrated in FIG. 5A and FIG. 5B, except for further including a fastening drive device 210, a communication unit 220, and an air vent 230, the splint 200 provided by this embodiment is basically the same as the splint 100 illustrated in FIG. 1A to FIG. 4.

For example, the splint 200 includes a fastening drive device 210, and the fastening drive device 210 includes a driver 211 and a fixer 212. For example, the driver 211 includes a motor 2111 and a rope spool 2112, and the fixer 212 includes a motor base 2121. The rope spool 2112 is connected to the rope 120, and the rope spool 2112 is capable of rotating under drive of the motor 2111 to allow the rope 120 to be twined on the rope spool 2112 or unwound from the rope spool 2112. The motor base 2121 is fixed on the first plate 111. The motor 2111 is disposed on the motor base 2121 and connected to the rope spool 2112, and is configured to rotate according to a driving signal to drive the rope spool 2112 to rotate, so as to allow the rope 120 to be tightened or loosened. For example, the motor 2111 is a servo motor.

For example, the splint 200 further includes a communication unit 220. The communication unit 220 is configured to receive a control signal that is wireless or wired and transmit the driving signal to the motor 2111. For example, the communication unit 220 is provided on one of the plurality of plates 110, for example, on the first plate 111. The communication unit 220 is in signal connection with the motor 2111 to transmit the driving signal, so as to allow the motor 2111 to rotate according to the driving signal, for example, rotate in the desired direction, angle, and rotation speed. For example, the communication unit 220 may be any applicable communication module or device, such as a Bluetooth module, an infrared communication module, a ZigBee module, etc., and the embodiments of the present disclosure are not limited in this aspect. The communication unit 220 may use a wired communication method or a wireless communication method. The wireless communication method can use any wireless communication protocol, such as Bluetooth, ZigBee, global system for mobile communications (GSM), wideband code division multiple access (W-CDMA), code division multiple access (CDMA), time division multiple access (TDMA), wireless fidelity (Wi-Fi), etc., and the embodiments of the present disclosure are not limited in this aspect.

For example, in an example, the communication unit 220 is a Bluetooth module, and is in Bluetooth connection with the mobile phone of the user who uses the splint 200. The user uses the application executing in the mobile phone to send a control signal through the Bluetooth function of the mobile phone, and after the communication unit 220 receives the control signal, the communication unit 220 transmits the driving signal to the motor 2111, so that the motor 2111 rotates in the desired direction, angle, and rotation speed, thereby implementing the function of controlling the degree of tightness of the rope 120.

For example, the splint 200 further includes an air vent 230. The air vent 230 is provided on one of the plurality of plates 110, for example, on the second plate 112. The air vent 230 can improve the ventilation performance of the splint 200 and increase the comfort of the user using the splint 200. The number of air vents 230 is not limited, and may be one or more, which may be determined according to practical requirements. The air vent 230 may be in any suitable shape such as a circle, a rectangle, and a square, and may be in any suitable size, which is not limited in the embodiments of the present disclosure. For example, the power supply 170 (not illustrated in FIG. 5A and FIG. 5B) may be provided on one of the plurality of plates 110, for example, on the second plate 112, as long as the power supply 170 keeps away from the air vent 230, and the embodiments of the present disclosure are not limited in this aspect.

The splint 200 can automatically adjust the degree of tightness of the rope 120 without manual adjustment, thereby saving time and effort, the adjustment speed is fast, and the adjustment efficiency is high, thereby improving the user's experience.

Figure 6:
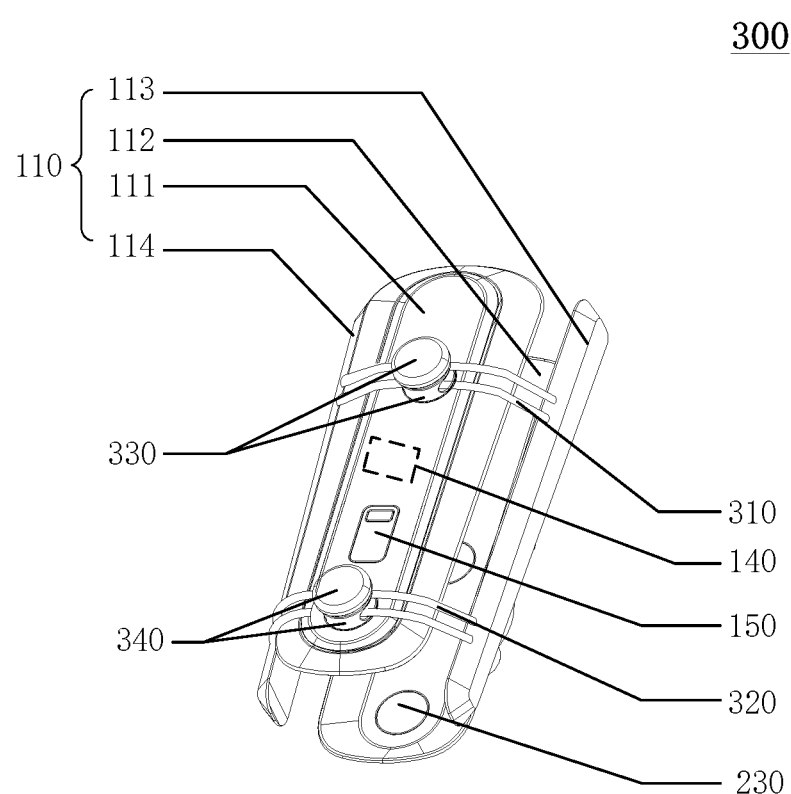
FIG. 6 is a schematic stereoscopic diagram of still another splint provided by at least one embodiment of the present disclosure.

FIG. 6 is a schematic stereoscopic diagram of still another splint provided by at least one embodiment of the present disclosure. As illustrated in FIG. 6, except that the numbers and connection method of the rope and the fastening drive device are different, and the air vent 230 is further included, the splint 300 provided by this embodiment is basically the same as the splint 100 illustrated in FIG. 1A to FIG. 4. The detailed description of the air vent 230 can be with reference to the above content, and details are not described herein again.

In this embodiment, the splint 300 includes a first rope 310, a second rope 320, a first fastening drive device 330, and a second fastening drive device 340. For example, the first rope 310 is in movable connection with the plurality of plates 110 in a parallel non-crossing manner, and the second rope 320 is also in movable connection with the plurality of plates 110 in a parallel non-crossing manner. The first rope 310 and the second rope 320 are independent from each other and do not cross each other. For example, the tension detecting circuit 140 can detect the tension of the first rope 310 and the tension of the second rope 320, respectively, and can display corresponding detection results on the display 150.

For example, the first fastening drive device 330 and the second fastening drive device 340 are both disposed on the first plate 111, and the first fastening drive device 330 and the second fastening drive device 340 are respectively connected to the first rope 310 and the second rope 320 in one-to-one correspondence. For example, the first fastening drive device 330 is connected to the first rope 310 and is configured to drive the first rope 310 under control, so that the first rope 310 can be tightened or loosened under drive of the first fastening drive device 330, so as to drive portions, which are connected to the first rope 310, of the plurality of plates 110 to move relatively close to each other or relatively away from each other. For example, the second fastening drive device 340 is connected to the second rope 320 and is configured to drive the second rope 320 under control, so that the second rope 320 can be tightened or loosened under drive of the second fastening drive device 340, so as to drive portions, which are connected to the second rope 320, of the plurality of plates 110 to move relatively close to each other or relatively away from each other.

The specific implementation manner of the first fastening drive device 330 and the second fastening drive device 340 can be with reference to the fastening drive device 130 in the splint 100 or the fastening drive device 210 in the splint 200 described above, and details are not described herein again. The specific implementation manner of the first fastening drive device 330 and the specific implementation manner of the second fastening drive device 340 may be the same or may be different, which is not limited in the embodiments of the present disclosure.

It should be noted that, in the embodiments of the present disclosure, the number of the ropes and the number of the fastening drive devices are not limited, and may be any values, such as 1, 3, 4, or the like, respectively, which can be determined according to practical requirements. For example, the number of the ropes can be equal to the number of the fastening drive devices, so as to better control the degree of tightness of the ropes.

In the splint 300, by using the first fastening drive device 330 and the second fastening drive device 340, the degree of tightness of the first rope 310 and the degree of tightness of the second rope 320 can be adjusted, respectively, which can reduce friction of the first rope 310 and the second rope 320 with the plurality of plates 110, thereby facilitating the balance of tension at both ends of each of the first rope 310 and the second rope 320, and extending the service life of the splint 300.

At least one embodiment of the present disclosure further provides a method for operating the splint according to any one of the embodiments of the present disclosure. The method can be used to operate the splint according to the embodiments of the present disclosure, which enables the user to adjust and fix the splint simply and quickly, thereby reducing user's workload, improving work efficiency, improving user's experience, and facilitating fixation of the splint. Moreover, the method provided by at least one embodiment can further monitor the degree of tightness.

For example, in an example, the method for operating the splint includes following operations: controlling the fastening drive device 130/210 to allow the rope 120 to be tightened or loosened, so as to allow the plurality of plates 110 to fit a using object or separate from the using object which is in a space surrounded by the plurality of plates 110.

For example, the using object is the injured limb of the patient, such as the leg, arm, etc. For example, in the case where there are a plurality of fastening drive devices and a plurality of ropes in the splint, the plurality of fastening drive devices can be respectively controlled to allow the plurality of ropes to be tightened or loosened, respectively.

For example, in another example, in the case where the splint 100/200 further includes a tension detecting circuit 140 and a display 150, the method for operating the splint further includes: adopting the tension detecting circuit 140 to detect a tension applied to the rope 120, and adopting the display 150 to display a tension detecting result of the tension detecting circuit 140.

For example, in the case where there are a plurality of fastening drive devices and a plurality of ropes in the splint, the tension detecting circuit 140 may be used to detect tensions of the plurality of ropes, respectively, and the display 150 may be used to display a plurality of tension detecting results of the tension detecting circuit 140.

It should be noted that, in the embodiments of the present disclosure, the method is not limited to the steps and sequence described above, and may further include more steps, and the execution sequence of these steps may be determined according to practical requirements, which is not limited in the embodiments of the present disclosure. The detailed description and technical effects of the method can be with reference to the descriptions of the splint 100/200/300 described above, and details are not described herein again.

The following statements should be noted.

(1) The accompanying drawings involve only the structure(s) in connection with the embodiment(s) of the present disclosure, and other structure(s) can be referred to common design(s).

(2) In case of no conflict, features in one embodiment or in different embodiments can be combined to obtain new embodiments.

What have been described above are only specific implementations of the present disclosure, the protection scope of the present disclosure is not limited thereto, and the protection scope of the present disclosure should be based on the protection scope of the claims.

What is claimed is:

1. A splint, comprising:
   a plurality of plates, comprising a first plate;
   at least one rope, in movable connection with the plurality of plates; and
   at least one fastening drive device on the first plate, connected to the rope and configured to drive the rope under control, so as to allow the rope to be tightened or loosened under drive of the fastening drive device to drive the plurality of plates to move relatively close to each other or relatively away from each other,
   wherein the rope comprises a core wire that is conductive and an insulating sheath, and a cross section of the core wire is deformable under a tension, so as to allow a resistance of the core wire to change.

2. The splint according to claim 1, further comprising a tension detecting circuit, wherein the tension detecting circuit is coupled to the rope and is configured to detect a tension applied to the rope.

3. The splint according to claim 2, further comprising a display, wherein the display is on one of the plurality of plates and in signal connection with the tension detecting circuit, and is configured to display a tension detecting result of the tension detecting circuit.

4. The splint according to claim 3, wherein the display comprises a display screen or a pointer instrument panel.

5. The splint according to claim 3, further comprising a power supply, wherein the power supply is on one of the plurality of plates and is configured to supply power to the tension detecting circuit and the display.

6. The splint according to claim 3, wherein the display is on the first plate.

7. The splint according to claim 2, further comprising a reminder device,
   wherein the reminder device is configured to perform a reminding operation in a case where a tension detecting result of the tension detecting circuit is less than a preset value.

8. The splint according to claim 1, wherein a material of the core wire comprises a piezoelectric ceramic fiber composite material or a conductive rubber.

9. The splint according to claim 1, further comprising a tension sensor, wherein the tension sensor is connected to the rope and is configured to deform under a function of a tension to allow a physical parameter of the tension sensor to change.

10. The splint according to claim 1, wherein the fastening drive device comprises a driver and a fixer,
    the driver is connected to the rope, the fixer is connected to the first plate, and the driver is movable relative to the fixer.

11. The splint according to claim 10, wherein the driver comprises a knob and a rope spool,
    the rope spool is connected to the rope, and the rope spool is capable of rotating along with the knob to allow the rope to be twined on the rope spool or unwound from the rope spool.

12. The splint according to claim 11, wherein the fixer comprises a fixing shaft, the fixing shaft is fixed on the first plate, and the knob is capable of rotating around the fixing shaft.

13. The splint according to claim 12, wherein the fastening drive device further comprises an electrical signal transmitter, the electrical signal transmitter comprises a first conductive ring, a second conductive ring, a first electrical brush, and a second electrical brush, both the first conductive ring and the second conductive ring are on the fixing shaft,
    the first electrical brush is electrically connected to a first end of the rope and is in frictional and electrical connection with the first conductive ring, and
    the second electrical brush is electrically connected to a second end of the rope and is in frictional and electrical connection with the second conductive ring.

14. The splint according to claim 13, wherein, in a case where the splint further comprises a tension detecting circuit, the tension detecting circuit is coupled to the rope and is configured to detect a tension applied to the rope, and the first conductive ring and the second conductive ring are coupled to the tension detecting circuit.

15. The splint according to claim 10, wherein the driver comprises a motor and a rope spool, the fixer comprises a motor base,
    the rope spool is connected to the rope and is capable of rotating under drive of the motor to allow the rope to be twined on the rope spool or unwound from the rope spool, and
    the motor is on the motor base and connected to the rope spool, and is configured to rotate according to a driving signal to drive the rope spool to rotate, so as to allow the rope to be tightened or loosened.

16. The splint according to claim 15, further comprising a communication unit, wherein the communication unit is configured to receive a control signal that is wireless or wired and transmit the driving signal to the motor.

17. The splint according to claim 1, wherein the at least one rope comprises a plurality of ropes, the at least one fastening drive device comprises a plurality of fastening drive devices, and the ropes are connected to the fastening drive devices in one-to-one correspondence.

18. The splint according to claim 1, wherein the rope is in movable connection with the plurality of plates in a parallel non-crossing manner or an S-shaped crossing manner.

19. A method for operating the splint according to claim 1, comprising:
    controlling the fastening drive device to allow the rope to be tightened or loosened, so as to allow the plurality of plates to attached to a using object or separate from the using object which is in a space surrounded by the plurality of plates.

\* \* \* \* \*